United States Patent [19]

Suzuki

[11] Patent Number: Plant 5,841

[45] Date of Patent: Dec. 30, 1986

[54] ROSE PLANT—KEITOLI VARIETY

[75] Inventor: Seizo Suzuki, Tokyo, Japan

[73] Assignee: The Conard-Pyle Company, West Grove, Pa.

[21] Appl. No.: 636,483

[22] Filed: Aug. 1, 1984

[51] Int. Cl.[4] ..... A01H 1/00

[52] U.S. Cl. ..... Plt./1

[58] Field of Search ..... Plt./1

*Primary Examiner*—R. E. Bagwill

*Attorney, Agent, or Firm*—Burns, Doane, Swecker & Mathis

[57] ABSTRACT

A new and distinct variety rose plant of the Shrub Class is provided which produces double pink blossoms in extreme abundance during the springtime which give a strikingly attractive overall appearance. The plant exhibits a distinctive weeping or semi-pendulous growth habit combined with extreme hardiness and excellent disease resistance.

19 Drawing Figures

SUMMARY OF THE INVENTION

The new and distinct variety of rose plant of the Shrub Class was created by artificial pollination wherein two parents were crossed which previously had been studied for the possession of the characteristics sought. The seed parent was an unnamed seedling of the Climber Class. The male parent was the Meihero variety (non-patented). The parentage of the new variety can be summarized as follows: Unnamed Climber × Meihero variety.

The seeds resulting from the above pollination were sown and plantlets were obtained which were physically and biologically different from each other. Selective study resulted in the identification of a single plant of the new variety. The desirable qualities of the new variety have been confirmed through extensive testing and the importance of the new variety has been firmly established.

It has been found that the new variety of rose plant of the Shrub Class possesses the following combination of characteristics:

(a) forms in abundance during the springtime on two year old wood small double blossoms which are empire rose shaded with geranium pink in coloration and which tend to be borne in clusters along the length of the stem,
(b) forms vigorous vegetation,
(c) exhibits a weeping or semi-pendulous growth habit,
(d) exhibits very good hardiness, and
(e) exhibits excellent disease resistance.

The new variety has been found to undergo propagation by various asexual means including budding. The characteristics of the new variety have been found to be strictly transmissible by such asexual propagation.

The rose plant of the new variety has been named the Keitoli variety.

BRIEF DESCRIPTION OF THE PHOTOGRAPH

The accompanying photograph shows as nearly true as it is reasonably possible to make the same in a color illustration of this character, typical specimens of plant parts of the new variety when grown during June. The rose plants of the new variety described herein were grown in Southern France (except as indicated hereafter) while outdoors and were grafted on *Rosa froebeli* rootstock.

Figures 1, 2, 3, 4, 5, 6, 7, 8, 9, 10, 11, 12, 13, 14, 15, 16, 17, 18:
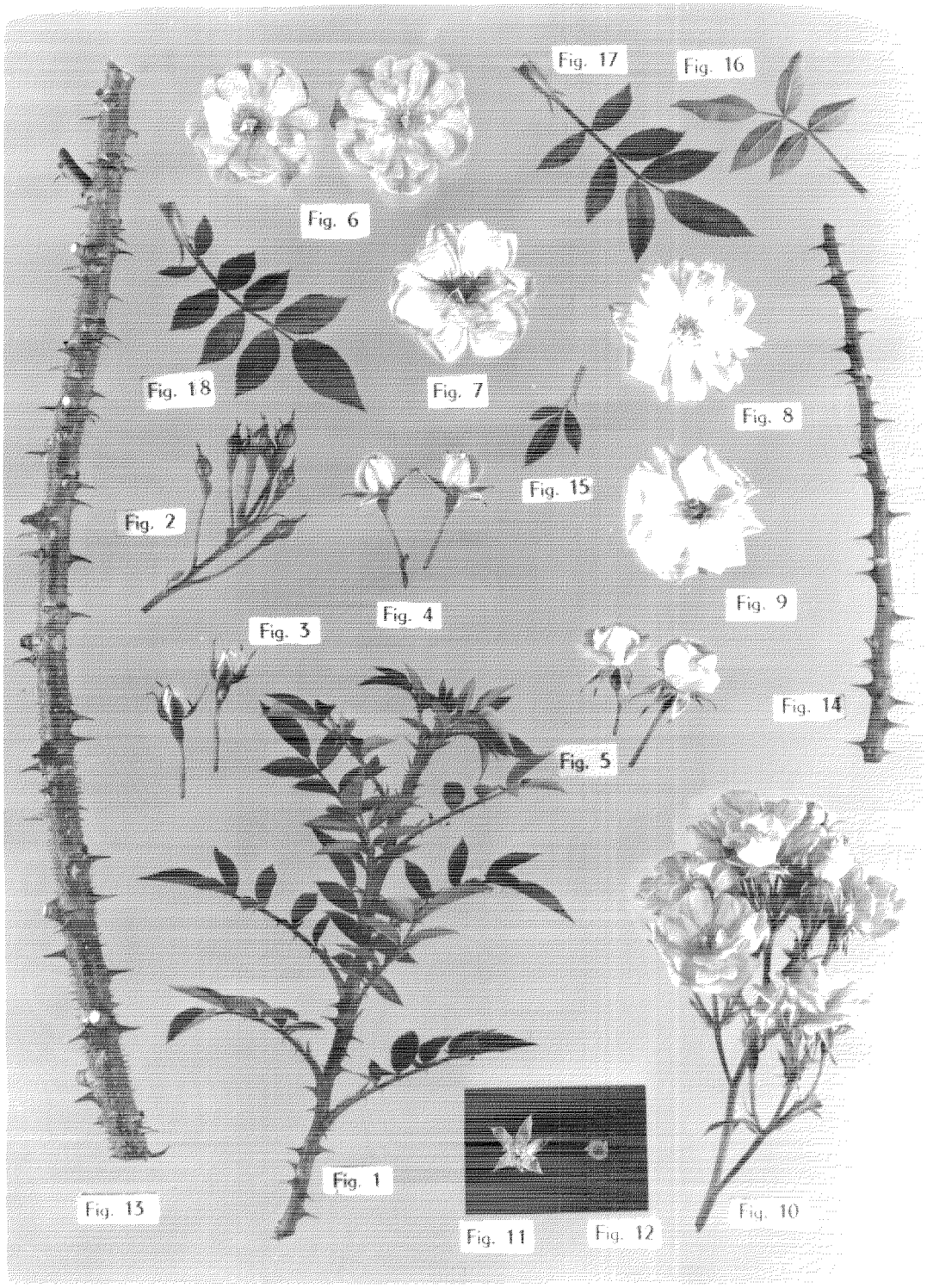
FIG. 1 illustrates a specimen of a young shoot.
FIG. 2 illustrates a specimen of a flowering bud before the opening of the sepals.
FIG. 3 illustrates a specimen of a bud at the opening of the sepals.
FIG. 4 illustrates a specimen of a flowering bud at the opening of the petals.
FIG. 5 illustrates a pair of flowers during the course of opening.
FIG. 6 illustrates a pair of fully open flowers—plan view—obverse.
FIG. 7 illustrates a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral stem with open blossoms.
FIG. 11 illustrates a specimen of a floral receptacle showing the arrangement of the stamens and pistils.
FIG. 12 illustrates a specimen of a floral receptacle showing the arrangement of the pistils (sepals and stamens removed)
FIG. 13 illustrates a specimen of a main stem.
FIG. 14 illustrates a specimen of a young flowering stem.
FIG. 15 illustrates a specimen of a leaf with three leaflets seen from above.
FIG. 16 illustrates a specimen of a leaf with five leaflets—under surface.
FIG. 17 illustrates a specimen of a leaf with seven leaflets—upper surface.
FIG. 18 illustrates a leaf with nine leaflets—upper surface.

It should be understood that the blossom coloration of the new variety is more accurately identified hereafter by reference to The R.H.S. Colour Chart than as illustrated in FIGS. 6 and 10.

FIG. 19 illustrates typical blossoms of the new variety in which the coloration is more accurately depicted than in FIGS. 6 and 10. On the top row of FIG. 19, the reverse side of typical fully open blossoms is illustrated. On the middle row of FIG. 19, the obverse side of typical fully open blossoms is illustrated. On the bottom row of FIG. 19, the obverse side of typical fully open blossoms is illustrated immediately prior to petal drop. The plants which produced the blossoms of FIG. 19 were grown outdoors at West Grove, Pa. during the summer.

DETAILED DESCRIPTION

The chart used in the identification of the colors is that of The Royal Horticultural Society (R.H.S. Colour Chart). The terminology preceding the numbered references has been added to designate in common terms the corresponding colors. The rose plants of the new variety described herein were grown in Southern France on *Rosa froebeli* rootstock and were observed during June.

Class: Shrub.

Plant:

*Height.*—Approximately 1.45 m. on average.

*Width.*—Approximately 1.70 m. on average.

*Habit.*—Weeping.

Branches:

*Color.*—Young stems: light green, Yellow-Green Group 143C. Mature wood: light green, Yellow-Green Group 143C.

*Thorns.*—Shape: Upper edge: straight and very thin, lightly inflected toward the base. Lower edge: slightly concave. Size: small. Quantity: few to moderate.

Leaves:

*Stipules.*—Large and linear.

*Petioles.*—Upper side: reddish brown on young foliage and light green on adult foliage. Under side: light green with several small thorns.

*Leaflets.*—Number: rarely 3, 5 and 7 (most often), and sometimes 9. Form: lanceolate. Serration: simple and regular. Texture: rough. General effect: foliage is very dense, ample, small and glossy. Color: young foliage: Upper surface: light green, Yellow-Green Group 144A. Under surface: light green, Yellow-Green Group 144C. Color: adult foliage: Upper surface: medium green, Yellow-Green Group 137B. Under surface: medium green, a little lighter than Yellow-Green Group 137D.

Inflorescence:

*Number of flowers.*—Clusters of approximately 22 to 27 flowers commonly are disposed on a single stem.

*Peduncle.*—Straight, rigid, and commonly has a length of approximately 1.9 cm. on average.

*Sepals.*—Upper surface: tomentose, greenish in coloration. Under surface: light green.

*Bud.*—Shape: ovate. Length: approximately 0.9 cm. on average. Size: small. Color: when opening: Upper surface: geranium pink, Red Group 43C, on the internal petals, and changing to geranium pink, Red Group 43D, on the external petals. Under surface: whitish and lightly tinted with fuchsia.

*Flower.*—Form: fully double, approximately 20 to 22 petals per blossom on the average not counting any small petals at the center which are less than one-half the size of the larger petals, initially fairly globular in configuration, but changes rapidly to a relatively flat configuration as the flower matures. Diameter: Approximately 3.7 cm. on average. Color: when opening begins: Upper surface: geranium pink, Red Group 43C, on the internal and external petals. Under surface: whitish and lightly tinted with fuchsia. Color: in course of opening: Upper surface: empire rose, Red Group 48C, lightly shaded with geranium pink, Red Group 43C, on the margin of the internal petals. Under surface: whitish and lightly tinted with fuchsia. Color: at end of opening: Upper surface: empire rose, Red Group 48D, more or less shaded with light empire rose, Red Group 48C on the margins of the petals. Under surface: whitish and lightly tinted with fuchsia. Fragrance: none. Lasting quality: long. Stamens: Number: approximately 120 on average. Anthers: normal and straw yellow in coloration. Pistils: Number: very difficult to count. Stigmas: greenish in coloration. Styles: very short and very close together, greenish in coloration. Receptacle: light green.

Development:

*Vegetation.*—Very vigorous.

*Flowering aptitute.*—Very abundant in spring on plants of two years old or more.

*Resistance to frost.*—Very good.

*Resistance to disease.*—Excellent.

I claim:

1. A new and distinct variety of rose plant of the Shrub Class which possesses the following combination of characteristics:

(a) forms in abundance during the springtime on two year old wood small double blossoms which are empire rose shaded with geranium pink in coloration and which tend to be borne in clusters along the length of the stem, (b) forms vigorous vegetation, (c) exhibits a weeping or semi-pendulous growth habit, (d) exhibits very good hardiness, and (e) exhibits excellent disease resistance, substantially as herein shown and described.

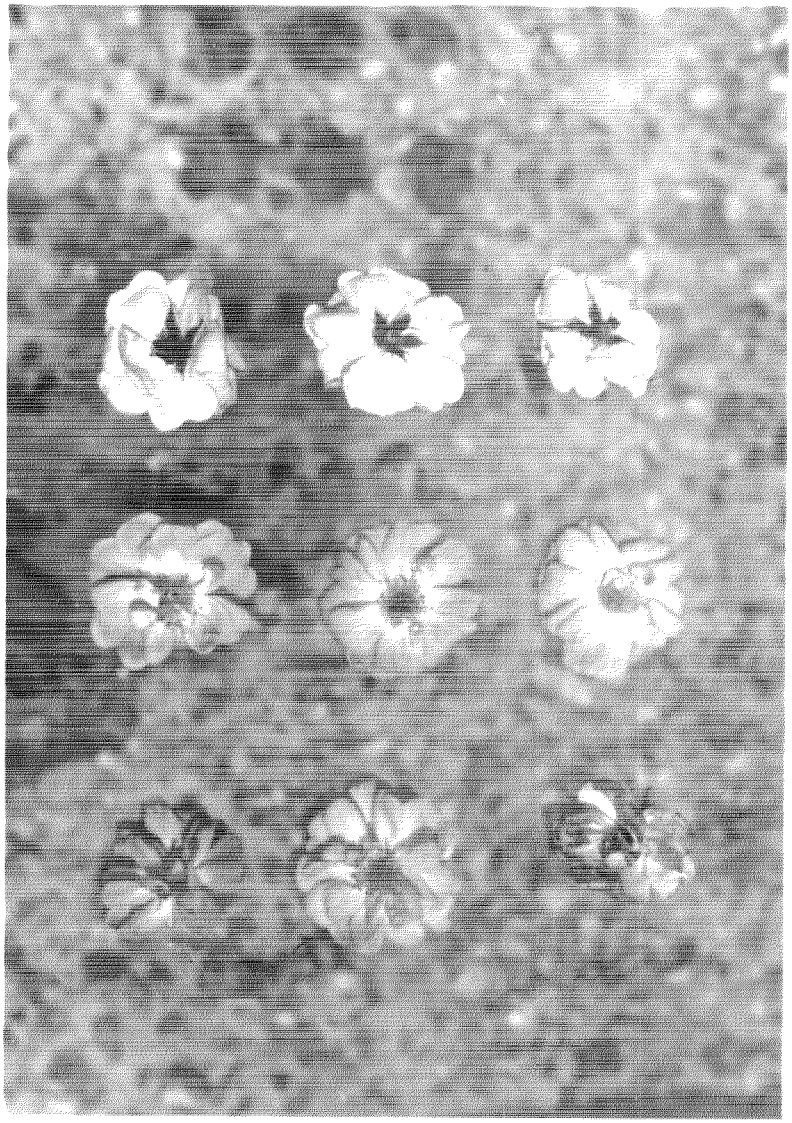

* * * * *